United States Patent [19]

Py

[11] Patent Number: 5,401,259
[45] Date of Patent: Mar. 28, 1995

[54] CARTRIDGE FOR APPLYING MEDICAMENT TO AN EYE

[76] Inventor: Daniel Py, 9 Hampden St., Wellesley, Mass. 02181

[21] Appl. No.: 132,621

[22] Filed: Oct. 6, 1993

Related U.S. Application Data

[63] Continuation-in-part of Ser. No. 863,943, Apr. 6, 1992, Pat. No. 5,267,986.

[51] Int. Cl.6 ............................................. A61M 35/00
[52] U.S. Cl. ........................... 604/294; 604/295;
604/300; 222/214; 222/336; 222/420
[58] Field of Search ............... 604/294, 295, 296, 297,
604/298, 299, 300, 301, 302; 222/23, 26, 214,
183, 336, 420

[56] References Cited

U.S. PATENT DOCUMENTS

| | | | |
|---|---|---|---|
| 3,563,415 | 2/1971 | Ogle | 222/420 X |
| 3,741,439 | 6/1973 | Vehrs. | |
| 3,993,064 | 11/1976 | McCarthy et al. | 604/294 |
| 4,471,890 | 9/1984 | Dougherty | 604/302 X |
| 4,623,337 | 11/1986 | Maurice | 604/298 |
| 4,634,023 | 1/1987 | Tanaka et al. | 222/214 X |
| 4,784,652 | 11/1988 | Wikstrom | 604/294 X |
| 4,792,334 | 12/1988 | Py | 604/295 X |
| 4,946,452 | 8/1990 | Py | 604/301 |
| 4,973,322 | 11/1990 | Jewart | 604/300 |
| 4,981,479 | 1/1991 | Py | 604/300 X |
| 4,982,875 | 1/1991 | Pozzi et al. | 222/420 X |
| 5,024,355 | 6/1991 | Jouillat et al. | 222/162 |
| 5,133,702 | 7/1992 | Py | 604/300 X |
| 5,154,702 | 10/1992 | Foyil | 222/420 X |
| 5,163,583 | 11/1992 | Whitworth | 222/420 X |

FOREIGN PATENT DOCUMENTS 9310852 6/1993 WIPO ........................... 604/295

Primary Examiner—Jerome L. Kruter
Assistant Examiner—Jones Mary Beth
Attorney, Agent, or Firm—Kenyon & Kenyon

[57] ABSTRACT

A cartridge for actuating a piston-like or accordion-like dispenser-vial for applying medicament to an eye. The cartridge includes a housing for holding the dispenser-vial and a telescoping cylinder for compressing the dispenser-vial in the longitudinal direction to actuate the vial. The cartridge includes a locking mechanism for locking the telescoping cylinder to restrict its movement and a lever mechanism for releasing the cylinder from the locked position so that a drop is released from the dispenser. The housing includes a finger for engaging the lower eyelid and exposing the conjunctival cul-de-sac.

23 Claims, 6 Drawing Sheets

CARTRIDGE FOR APPLYING MEDICAMENT TO AN EYE

This application is a continuation-in-part of Ser. No. 07/863,943, filed on Apr. 6, 1992, now U.S. Pat. No. 5,267,986.

BACKGROUND OF THE INVENTION

1. Field of the Invention

The invention relates to a cartridge for applying medicament to an eye from a vial-dispenser of the type which is actuated by compression of the vial between its nozzle and its bottom wall.

2. Description of Related Art

There are various dispensers which are known for applying medicament to an eye. A typical eye-drop container includes a flexible vial storage portion and a nozzle for dispensing drops of medicament into the eye by squeezing the vial between its side walls. Less common, but more precise, are accordion-like or piston-like dispensers which are actuated by squeezing the vial between a bottom wall and the nozzle so as to compress the vial in its longitudinal direction, rather than from its sides. It is these accordion-like or piston-like dispensers with which the cartridge of the present invention is particularly adapted for use. An example of a new and improved piston-like dispenser which propels microdrops into the eye is the subject of my U.S. application Ser. No. 07/801,243 which is expressly incorporated herein by reference.

Most people encounter difficulty in applying drops to their eyes. The eye is a very sensitive body part and individuals find it difficult to control reflexive blinking when applying drops thereto. Also, eye drop users often have poor vision. Poor vision makes it difficult to position the tip of the dropper bottle over the eye and frequently causes drops to be incorrectly applied to the nose or cheek. Additionally, elderly people often have difficulty holding a dropper bottle steady or encounter difficulty in squeezing the bottle to apply a proper quantity of the medicament.

Even if the liquid medicament is properly applied to the eye, the medicament's effectiveness is limited. The minimum volume of a drop of liquid medicament which can ordinarily be introduced into contact with an eye at one time is about 30 $\mu$l. Any amount which is greater than about 25 $\mu$l usually spills over the eyelid onto the cheek since this is the maximum volume which the eye can ordinarily handle. When eye drops are applied to the surface of the eyeball, blinking and natural tear flow combine to limit the time to a few minutes that liquid medicament will remain effective.

On the other hand, if medicament is applied to the cul-de-sac of the conjunctiva, the medicament will remain effective for a longer period of time, maximizing the benefits of applying drops of liquid medicament to the eye. This is because the conjunctiva is an area of low sensitivity and low tear turnover such that blinking and tearing are avoided. However, because of the difficulty encountered in steadying the dropper and accurately positioning it over the conjunctiva, maximizing the effectiveness of the medicament remains elusive.

U.S. Pat. No. 4,543,096 describes and illustrates an apparatus having finger-like projections which are attached to the front of an eye drop bottle to spread the eyelids apart during the eye drop dispensing process. One moveable finger is connected to a lever for both depressing the lever and simultaneously causing the eyelids to spread apart while forcing a drop from the dropper bottle. However, the apparatus described in U.S. Pat. No. 4,543,096 cannot be used with the accordion-like or piston-like dispensers which are actuated by compression in the longitudinal direction rather than from the sides. Furthermore, this apparatus will not properly expose the cul-de-sac.

Similarly, U.S. Pat. No. 4,531,944 depicts an apparatus for steadying the tip of a dropper over the eye and further includes a sighting hole to distract the eye. However, this apparatus does not have a means to expose the cul-de-sac nor keep the lower eyelid depressed.

Typical eye-drop dispensers also have the disadvantage that the force which is necessary to actuate the dispenser to emit a drop is not in the same direction as the motion which is necessary to lower the lower eyelid and expose the cul-de-sac. It would be desirable to have a device which actuates the dispenser with a motion which is in the same direction as that which is necessary to lower the lower eyelid.

U.S. Pat. No. 5,267,986 describes a device which meets all of the above-described needs. Additional improvements and variations on this device are described herein.

SUMMARY OF THE INVENTION

It is an object of the invention to provide a device which can accurately deliver a small drop of medicament to the conjunctival cul-de-sac of an eye.

It is a further object of the invention to provide such a device which can be used to actuate an accordion-like or piston-like vial-dispenser using minimal force.

It is a further object of the invention to provide such a device wherein the motion used to actuate the dispenser to emit a drop is in the same direction as the motion which is necessary to depress the lower eyelid and expose the conjunctival cul-de-sac.

It is a further object of the invention to provide a device having these features which has a simple construction and which is easy to manufacture.

The foregoing objects are achieved by the present invention which provides a cartridge which is particularly adapted for actuating an accordion-like or piston-like dispenser-vial. The cartridge includes a generally elongated housing which is adapted to receive a dispenser-vial between an anterior wall of the housing and a telescoping cylinder. The anterior wall of the housing has an aperture for exposing the nozzle of the vial. The anterior of the housing may be provided with a cover, shutter or the like for closing the opening. The nozzle is preferably receded within the housing so that it does not project out of the opening so as to prevent any corneal injury in the event of accidental contact with the eye.

The back of the housing has an opening which slidably receives the telescoping inner cylinder. When the inner cylinder is pushed toward the anterior of the housing it forces the dispenser-vial to compress in the longitudinal direction between the anterior wall of the housing and the cylinder. In the case of some dispensers which can be used with the invention, compression causes a drop of liquid medicament to enter the drop cavity of the dispenser thereby "loading" the drop cavity.

The top of the inner cylinder has a surface defining one or more upwardly projecting teeth which are especially adapted to engage with an opposing tooth on a lever, to lock the inner cylinder in a plurality of different positions. Each tooth includes at least a first surface which is inclined with respect to the top surface of the inner cylinder, and a second surface which extends from the top of the first surface at an acute angle therewith toward the top surface of the inner cylinder where it terminates with the top surface, preferably at about a right angle. Thus, from the side, each tooth resembles a right triangle.

The lever is preferably a fork having a pair of prongs (i.e., an upper prong and a lower prong) and a lever arm. The lever arm has a tooth which substantially corresponds in shape to the type of tooth belonging to the inner cylinder. The tooth of the lever arm extends downwardly in opposed relationship to the upwardly extending teeth of the inner cylinder. An upper prong is angled in the upward direction from a pivot point of the lever, and includes a raised area which defines a button. The button is exposed or projects out through an aperture in the top of the housing. A lower prong angles downwardly from the pivot point to come into contact with and rest upon a shelf which projects from the anterior wall or side wall of the housing toward the interior of the housing.

When the posterior end of the inner cylinder is pushed anteriorly (i.e., toward the interior of the housing), the inclined surface of the tooth belonging to the inner cylinder will slide over the inclined surface of the tooth belonging to the lever arm and, in so doing, will urge the lever arm upward until the inclined surface of the tooth belonging to the inner cylinder has passed by the inclined surface of the tooth belonging to the lever arm. At this point, the lever arm will snap back downward due to the force exerted by the two prongs which are wedged between the shelf and the top wall of the housing. As the lever arm snaps downward, the second (e.g., normal) surface of its tooth will engage with the second surface of the tooth belonging to the inner cylinder, thereby locking the inner cylinder in place. In the case of some dispensers which can be used with the invention, the resulting compression of the dispenser in the cartridge causes a drop of liquid medicament to enter a drop cavity of the dispenser, thereby "loading" the drop cavity.

Upon depression of the button belonging to the upper prong of the lever, the lever arm will be forced upward about the pivot point of the lever, and the second (e.g., normal) surface of its tooth will disengage from the second surface of the tooth belonging to the inner cylinder. Upon disengagement, the inner cylinder will be urged posteriorly (i.e., in the direction out of the housing) by the action of a bellows, spring or other biasing means which continually urges the inner cylinder to expand in the longitudinal direction, said expansion causing the posterior end of the inner cylinder to project out of the posterior end of the housing. The biasing means may belong to the inner cylinder itself, as well as to the dispenser. With some of the dispensers which can be used with the invention, decompression causes the drop of liquid which had previously entered the drop cavity to be emitted through the nozzle.

Movement of the inner cylinder in the posterior direction is restricted by engagement of the second surface of the tooth belonging to the lever with the second surface of a second tooth belonging to the inner cylinder. Alternatively, or in addition, movement of the inner cylinder in the posterior direction may be restricted by cooperation between a posterior wall of the housing and a widened section of the inner cylinder which cannot fit through the opening in the posterior wall of the housing, or by a stop member in the housing which engages a tooth on a lower surface of the inner cylinder.

For additional leverage, the lever may include a pair of laterally extending pins at the point where the upper and lower prongs meet with the lever arm (i.e., the pivot point). The laterally extending pins fit into corresponding bearings which are fixed to the interior of the housing. The lever will then be pivotable about these pins which are rotatable in the bearings.

The lower section of the anterior section of the housing is formed with a soft finger which is adapted to engage the lower eyelid. Alternatively, the finger is a projection formed of the same material as the housing which can receive a sleeve of a soft material.

In order to apply a drop of medicament, the inner cylinder is pushed into its locked position to load the dispenser-vial. The nozzle is then positioned over the eyeball with the finger pressing on the lower eyelid to expose the conjunctival cul-de-sac. When the button is depressed the resulting motion of the cartridge will be in the same direction as the motion which causes the finger to lower the lower eyelid and expose the conjunctival cul-de-sac as a drop is emitted.

BRIEF DESCRIPTION OF THE DRAWINGS

FIG. 9 is an isolated view of a side wall of the housing and a bearing.

DETAILED DESCRIPTION OF THE INVENTION

Figure 5:
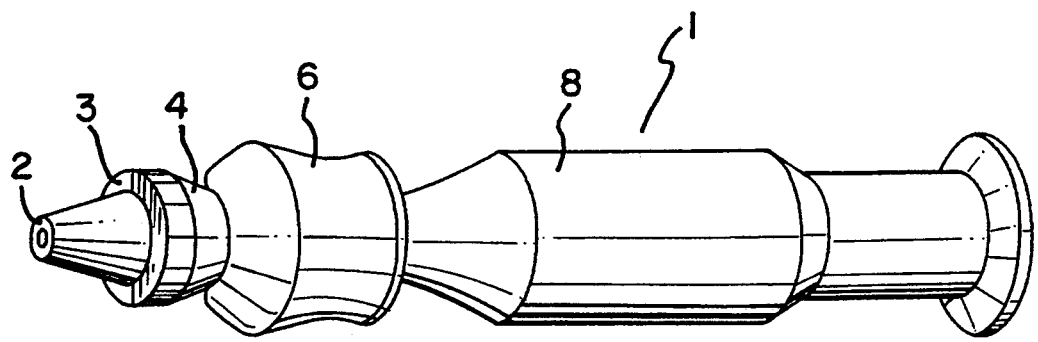
FIG. 5 is a perspective view of a dispenser-vial which can be used in the cartridge of the invention.
Figure 8:
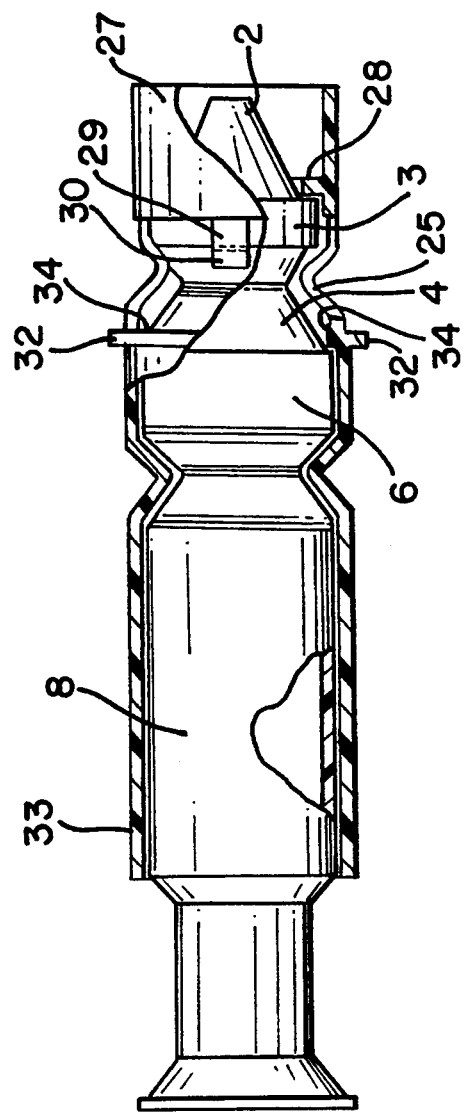
FIG. 8 is a cross-sectional side view of the inner compressible member containing the dispenser vial depicted in FIG. 5.

The cartridge of the invention is specially adapted to work in conjunction with an accordion-like or piston-like dispenser-vial. An example of a new and improved piston-like dispenser which can be used in the cartridge of the invention is the subject of my application Ser. No. 07/801,243 which is expressly incorporated herein by reference, however, the present invention is not limited to use with this particular dispenser. Parts of a dispenser described in application Ser. No. 07/801,243 which are relevant to an understanding of the present invention are illustrated in FIGS. 5 and 8 and will now be described briefly to facilitate understanding of the cartridge.

The dispenser-vial generally depicted at 1 includes a nozzle 2, wing 3, a bellows portion 4, wing 6 and a rear vial section 8 containing a storage supply of liquid medicament. The dispenser is compressible in the longitudinal direction along the bellows. For this purpose, the bellows portion 4 is constructed of a soft flexible plastic material such as the thermoplastic resin sold under the trademark Kraton from the Shell Company. Resiliency of the dispenser can be provided by the spring quality of the accordion bellows made of "Kraton". "Kraton" has an excellent memory and can be an excellent spring. Alternatively, resiliency may also be provided by a longitudinally disposed spring (not illustrated) which urges the dispenser to expand upon compression.

The dispenser includes a drop cavity therein (not illustrated) which holds a predetermined volume of fluid to be emitted in the form of a drop. Compression of the dispenser in its longitudinal direction creates a drop in pressure in the drop cavity to fill or "load" the drop cavity with liquid where it is stored until it is emitted as a drop from the nozzle 2. This compressed state will be referred to herein as the loaded state. Expansion of the dispenser from the loaded state (caused by the bellows-spring) urges the fluid in the drop cavity under pressure toward the nozzle 2 from which it is emitted in the form of a drop. It can be seen that the force which is required to actuate this type of dispenser must ordinarily be applied in the direction of the nozzle. With this background information about the operation of the piston-like dispenser in mind, the cartridge of the invention will now be described.

Figure 1:
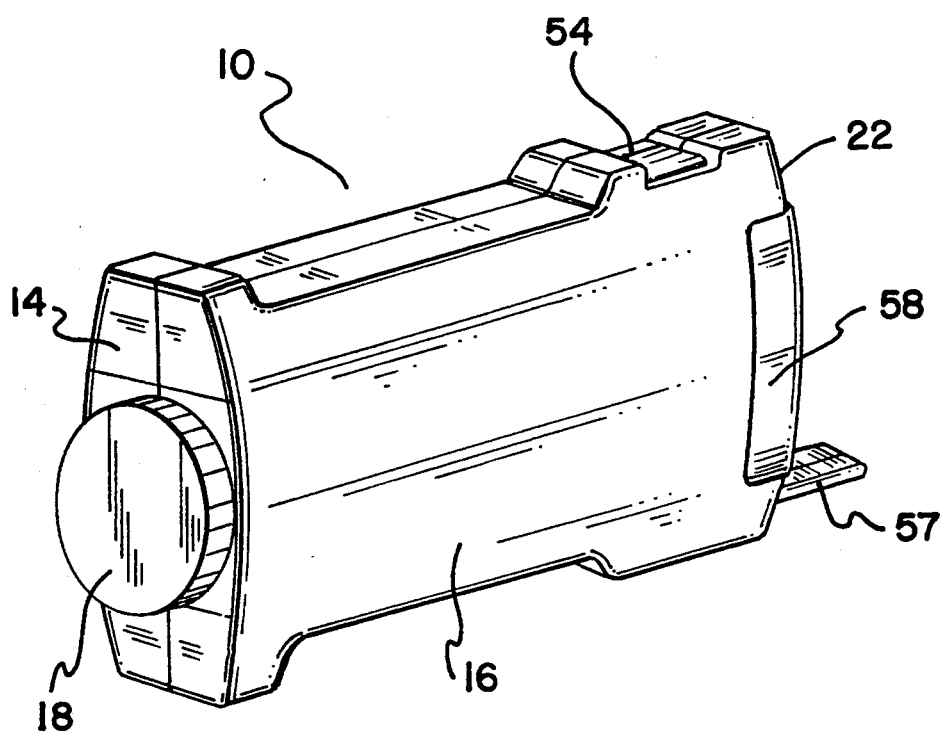
FIG. 1 is a perspective view of a cartridge in accordance with the invention.
Figure 2:
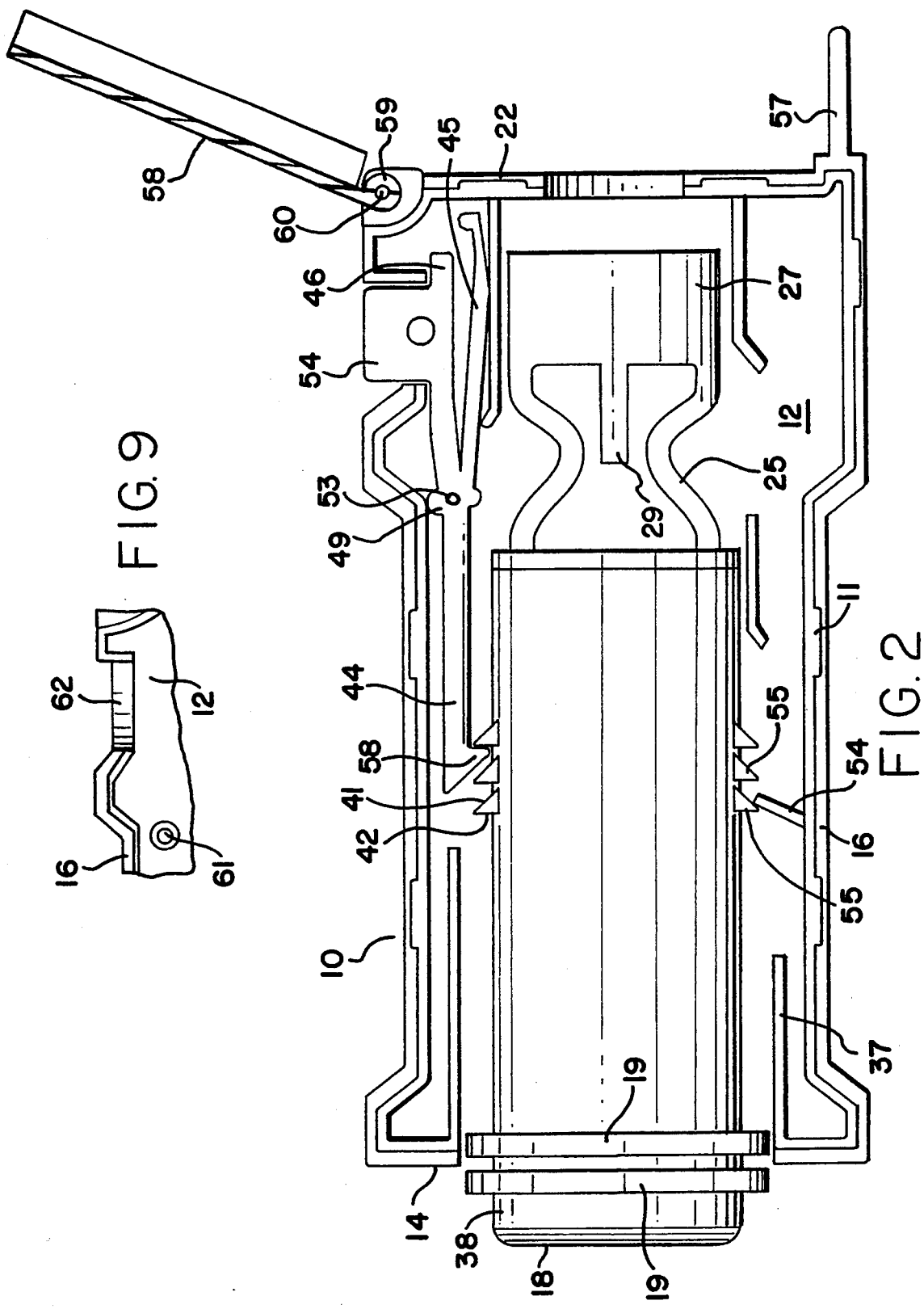
FIG. 2 is a detailed cross-sectional side view of a cartridge in accordance with the invention in a shelf life, rest position.

Referring to FIGS. 1 and 2, the cartridge, which is generally indicated at 10, includes a housing 16 which may be cylindrical or any other convenient shape to be hand held. The housing 16 includes side walls 12 and a posterior wall 14 which slidably receives an inner compressible member 18, which may be cylindrical, through a posterior aperture 20 therein. The posterior wall 14 has a close tolerance with respect to the inner cylinder 18 to help close off the housing to the external environment. For this purpose, the posterior section of the inner compressible member 18 may include one or more ribs 19 whose shape matches that of the posterior aperture 20, the ribs being positioned so that they fit flush against the posterior wall 14 to close aperture 20 in the rest position of the cartridge.

The front of the housing 16 is substantially closed by an anterior wall 22 which has an aperture 24 centrally located therein allowing for the exposure of the nozzle 2 of the dispenser. Preferably, the cartridge is dimensioned such that a dispenser can fit snugly therein with its nozzle completely receded within the aperture 24 of anterior wall 22. In this way, accidental contact of the nozzle with the eye is not possible, which avoids injuries, as well as contamination of the outside of the nozzle.

The inner cylindrical member 18 includes a spring or bellows portion 25. The spring 25 is situated between a posterior section 26 of the cylindrical member and an anterior section 27 of the cylindrical member. When the medicament dispenser 1 is mounted in the cartridge, it is first fit within the inner cylindrical member 18 in the manner which will be described hereinafter. Since the wing 6 of the dispenser 1 must be compressed in the longitudinal direction to become loaded, it must be somehow fixed within the inner cylindrical member 18. For this purpose, the anterior section 27 includes an inwardly projecting rim 28 which engages the wing portion 3 of the dispenser (see FIGS. 7 and 8). The rim 28 is disposed anteriorly to the wings 3 to prevent the wings from moving forward when the inner cylindrical member 18 is pushed inward, as will be described hereinafter. The anterior section 27 of the inner cylindrical member 18 preferably also includes a pair of posteriorly extending projections 29, each projection having a tooth 30 at the posterior end thereof. The distance between each tooth 30 and the rim 28 should approximate the width of the wing 3, such that the wing 3 can be wedged snugly between the teeth 30 and the rim 28. The cooperation of teeth 30 and rim 28 will maintain the dispenser 1 in the inner member 18 in a fixed position suitable for compression as well as expansion.

Figure 6:
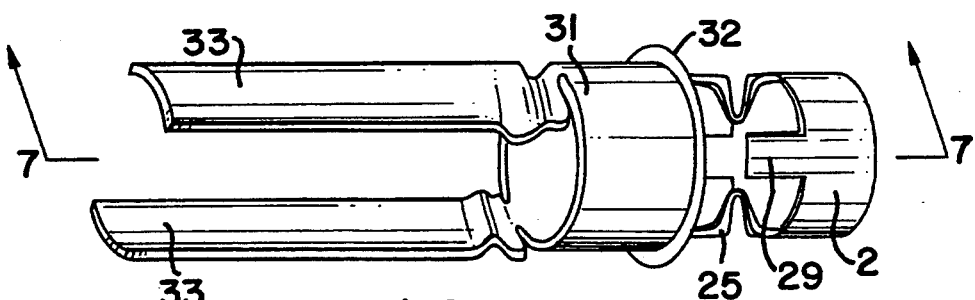
FIG. 6 is a perspective view of an anterior section and insert portion of the inner compressible member of the cartridge of the invention.
Figure 7:
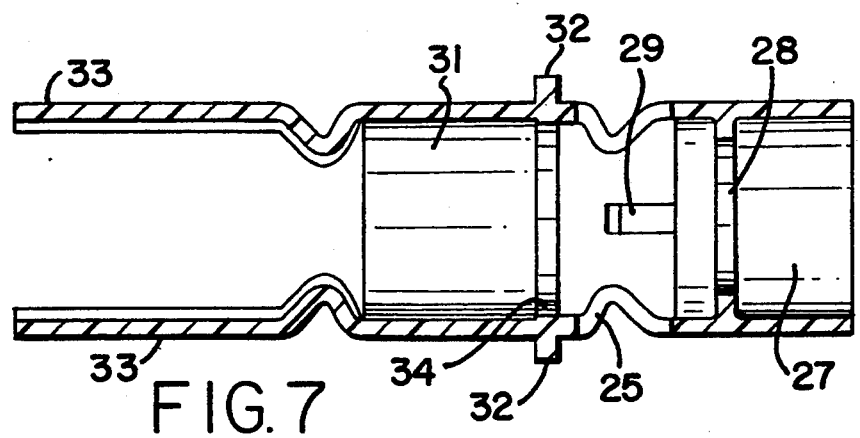
FIG. 7 is a cross-sectional view of the anterior section and insert portion depicted in FIG. 6 taken along the line 7—7.

The posterior end of the spring portion 25 is connected to an insert member 31 (see FIGS. 6–8). The insert member 31 is adapted to fit into an anterior opening of the posterior section 26 of the inner cylindrical member 18. The insert portion 31 has an outwardly projecting rim 32, which engages the posterior section 26 for defining the limit of motion of the insert portion in the opening of the posterior section 26. The insert portion 31 includes two posteriorly projecting tab portions 33 which fit around the vial section 8 of the dispenser. The insert portion 31 also includes an inwardly projecting rim 34 which engages the wing 6 of the dispenser 1 when the dispenser is inserted into the inner cylindrical member 18. Preferably, the anterior section 27, spring 25, projections 29, insert portion 31 and tabs 33 are integrally molded as a single structure, separate and apart from the posterior section 26 of the inner cylindrical member.

Figure 10:
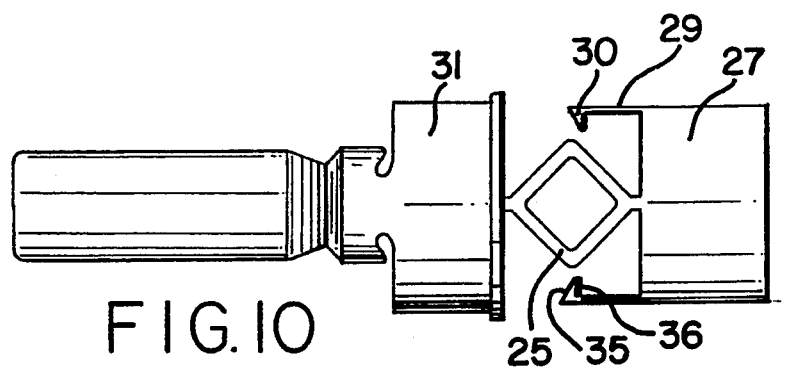
FIG. 10 is a side view of an anterior section and insert portion of the inner compressible member of the cartridge of the invention, which is rotated 90° from the view of FIG. 6.

The dispenser 1 is easily inserted into the inner cylindrical member 18 of the cartridge of the invention as follows. The anterior section 27, spring 25, insert member 31 and tabs 33 are separable from the posterior section 26 of the inner cylindrical member 18. The nozzle 2 of the dispenser is fed through the tabs, through the insert portion 31 through the inwardly projecting rim 34, between the spring members 25, between the projections 29 and through the rim 28 toward the anterior end of the anterior section. The space defined inside the rim 34 is large enough to allow the wing 3 to clear passed it. Each tooth 30 (see FIG. 10) has an inclined surface 35 which allows the wing 3 to slide over each tooth as the dispenser is fed into the anterior section 27 as described above. However, each tooth also has a surface 36 which is normal or otherwise angled to the projection 29 to which it belongs to act as a stopper for preventing wing 3 from passing over it so as to retain the dispenser in the anterior section 27. This normal surface 36 is anterior to the inclined surface 35 and will engage the wing 3 once the wing 3 has slid passed the teeth. It will be appreciated that the pair of projections 29 will flex outwardly as the wing 3 slides passed the teeth. However, the projections 29 will snap back inwardly once the wing 3 has cleared the teeth. The wing 3 will now be held in place between the rim 28 and the surfaces 36 of the teeth 30 (see FIG. 8). In this position, the wing 6 of the dispenser will engage the inward rim 34 of the insert portion 31, and the tabs 33 will be positioned around the vial section 8 of the dispenser (see FIG. 8).

The anterior section 27, spring 25 and insert portion 31, having the dispenser 1 locked therein, are now ready to be coupled to the posterior section 26 of the inner cylindrical member 18. The tabs 33 facilitate guiding of the combination dispenser and anterior section into the posterior section 26. The insert member 31 is completely inserted within the posterior section 26 when the outwardly projecting rim 32 engages the posterior section 26. The posterior end of the posterior section 26 is closed to provide an additional barrier for the vial portion 8 of the dispenser against the external environment (e.g., oxygen, water moisture, $CO_2$, etc.).

The thus assembled inner telescoping member 18 containing the dispenser is situated within the housing 16. Preferably, the spring portion 25 of the inner cylindrical member 18 is a flexible, but resilient, plastic material which, when compressed in the longitudinal direction, will exert an expanding force. The housing 16 may be molded by conventional plastic molding techniques, and is preferably molded as two, snap-fittable half sections along its longitudinal axis so that the inner cylindrical member 18 containing the dispenser 1 may be easily situated therein. The two half sections are molded by conventional techniques so that they can be securely snapped together (e.g., by engagement of snap-fit members 11 on one of the half sections into female receptors (not illustrated) on the other half section to close the housing.

The interior of the housing 16 includes a pair of retaining-guiding shelves 37 which project from the side walls 12 to the interior of the housing. The shelves 37 function to guide the inner cylindrical member 18 for compression and expansion in the longitudinal direction within the housing, but restrict any movement in directions transverse to the longitudinal axis. The inner cylindrical member 18 is mounted between the anterior wall 22 and the posterior wall 14 of the housing, with a portion 38 of the inner member 18 projecting outside of the housing through the posterior aperture 20 in the rest state.

The top surface of the posterior section 26 of the inner compressible member 18 defines one or more teeth 40 which, in cooperation with an opposing tooth 50 of a lever 43, allow for the adjustment of the inner compressible member 18 to various positions. Each tooth 40 includes at least a first surface 41 which is inclined with respect to the top surface of the posterior section 26, and a second surface 42, which extends from the end of the first surface 41 toward the posterior section 26 to define an acute angle with the first surface 41. Preferably, the second surface 42 is about normal to the top surface of the posterior section 26.

The cartridge includes a lever generally depicted at 43 for releasably locking the inner compressible member 18 in a variety of different positions. The lever 43 includes a lever arm 44, a lower prong 45 and an upper prong 46. The lower and upper prongs 45, 46 are wedged between shelf 47 and top wall 48, respectively, of the housing 16. Shelf 47 projects inwardly from the side wall 12 and/or the anterior wall of the housing. The prongs 45, 46 are joined to the lever arm 44 at a pivot point 49. The posterior end of the lever arm 44 defines a tooth 50 which has substantially the same configuration as the teeth 40 belonging to the inner compressible member 18. Tooth 50 has a first, inclined surface 51 which is angled so as to be able to make smooth sliding contact with inclined surface 41 of tooth 40. Tooth 50 also has a second surface 52 which is adapted to engage the second surface 42 of one of teeth 40. Preferably, second surface 52 is about normal to the lever arm 44, but in any event is angled so as to engage the second surface 42 of tooth 40 to prevent that surface from sliding past it.

The pivot point 49 of the lever 43 includes a pair of laterally extending pivot pins 53. Each pivot pin 53 is adapted to be rotatably received within a bearing 61 (see FIG. 9) provided on the interior of the side walls 12 of the housing 16. The pivot pins 53 are rotatable within the bearings for allowing the lever to pivot about the pivot point 49.

The upper prong 46 of the lever 43 includes an elevated section 54 for use as a push button. The push button 54 is exposed to the user through an opening 62 (see FIG. 9) in the top of the housing 16.

Figure 3:
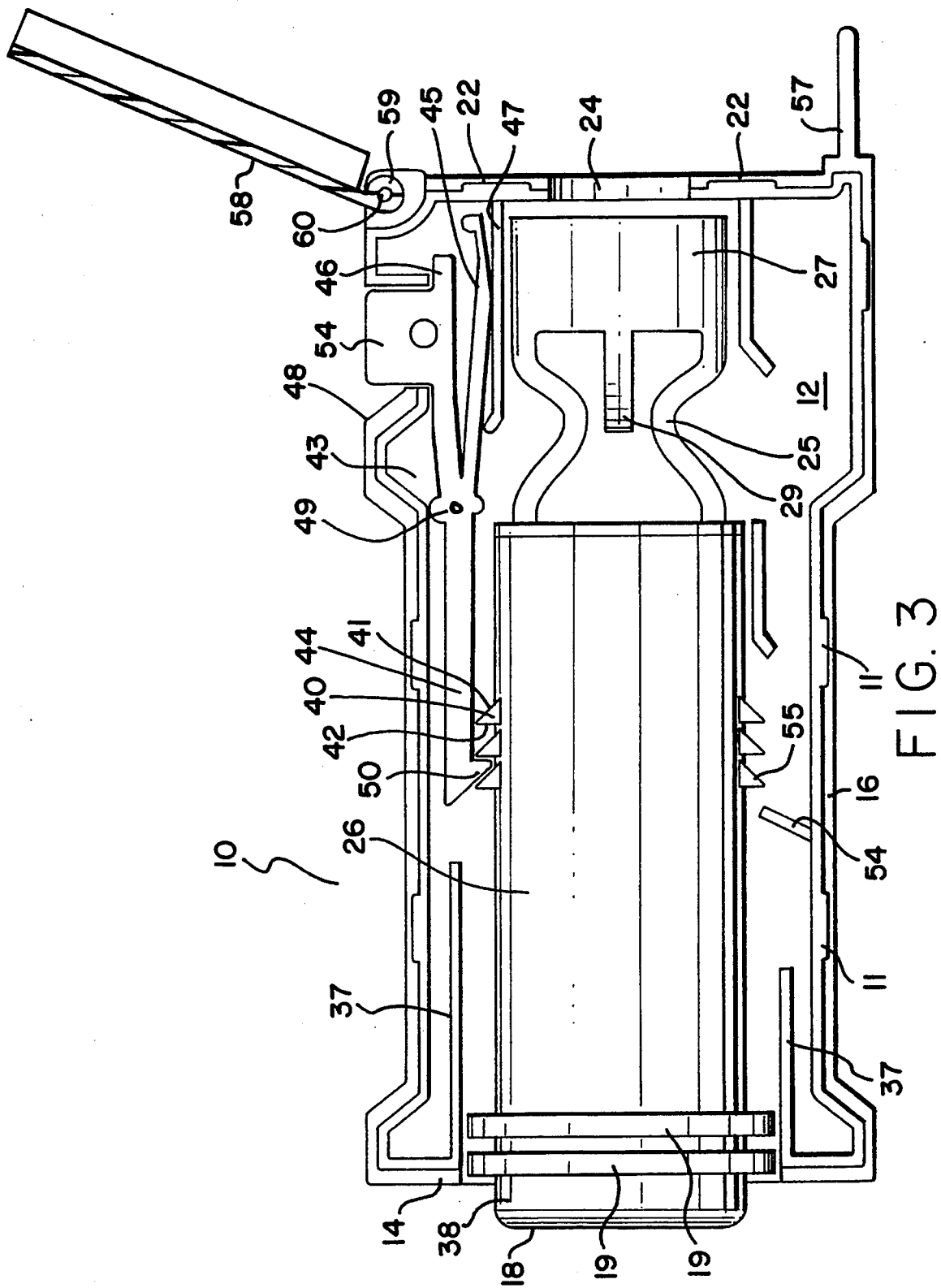
FIG. 3 is a detailed cross-sectional side view of the cartridge in a normal rest position.

The significance of the structure of the teeth 40 and 50, and the cooperation thereof, will now be explained with reference to the operation of the cartridge. Referring to FIG. 3, the cartridge is illustrated in the rest position. In this position, it can be seen that the second surface 52 of tooth 50 acts as a stop member for preventing the second surface 42 of one of the adjacent, anteriorly positioned teeth 40 from traversing over it in the posterior direction, thereby preventing the inner compressible member 18 from sliding out of the housing 16 through the posterior aperture 20. For this purpose, a stop member 54 may also be provided on the bottom of the housing 16 for engaging teeth 55 which may be optionally provided on the bottom surface of the posterior section 26.

Figure 4:
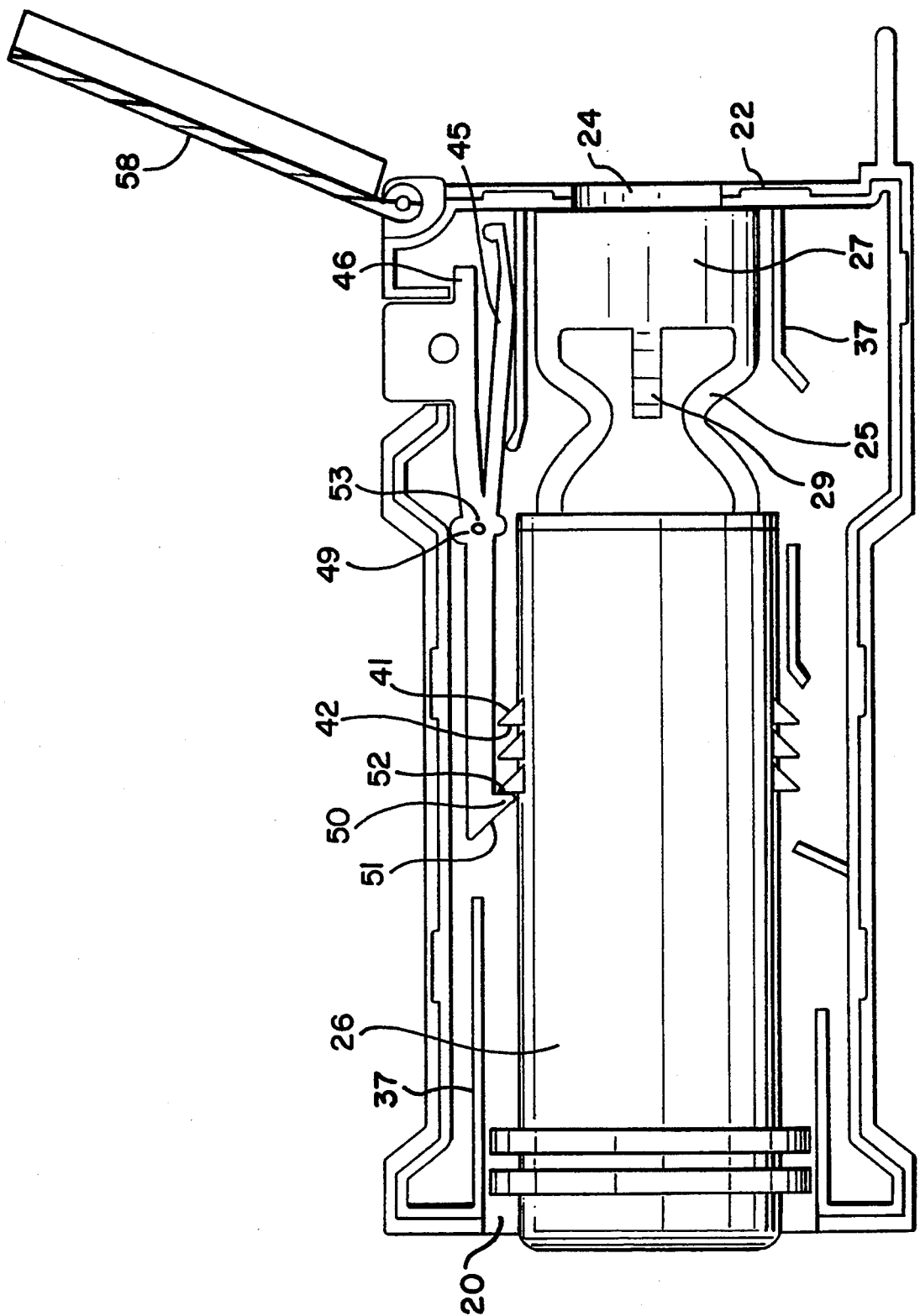
FIG. 4 is a detailed cross-sectional side view of the cartridge in a loaded position.

In order to load the dispenser 1 contained in the inner member 18, the user presses on the posterior end of the inner compressible member 18 to force it to compress in its spring region 25 in the housing 16. During this motion, the first surface 41 of the most posterior of the teeth 40 will slide over the first surface 51 of tooth 50 of the lever 43. In so doing, the lever arm 44 will be forced to pivot upwardly until surface 41 clears surface 51. At this point, the lever arm 44 will be free to snap back into its original position, resulting in engagement of surface 42 of the most posterior tooth 40 with surface 52 of tooth 50. As explained above, the engagement of surface 42 with surface 52 locks the inner member 18 in position. This is the loaded position which is illustrated in FIG. 4, wherein the spring or bellows 25 is compressed. It is in this position that a drop of medicament has been loaded into the drop cavity of the dispenser 1 as described above.

In order to emit the drop, the user simply depresses push button 54 of the upper prong 46 of the lever 43. This will result in the lever arm 44 pivoting upward about the pivot point 49, until surface 52 has cleared surface 42 of the most posterior tooth 40. The inner compressible member 18 will then be free to expand by the force exerted by the spring 25 (and bellows 8 of the dispenser) back to its rest position illustrated in FIG. 3. Upon expansion of the bellows portion of the dispenser 1 in the compressible member 18, a drop of medicament will be emitted from the nozzle as discussed above.

The inner compressible member 18 may be formed with three teeth 40 in order to allow for the cartridge to originally (i.e., prior to first use) assume a third position, which will be referred to as a shelf life position. The optional third tooth is the most anterior of the teeth 40 illustrated in FIGS. 2-4. The shelf life position is illustrated in FIG. 2 where it can be seen that the tooth 50 is wedged between the most anterior of the teeth 40 and the middle of the teeth 40. In this position, the inner compressible member 18 projects out from the posterior aperture 20 to a greater extent than in the rest position illustrated in FIG. 3, and the anterior end 56 of the anterior section 27 of the inner compressible member 18 is spaced away from the anterior wall 22. Thus, if someone were to accidentally push in the inner compressible member 18, the spring 25 would not initially compress because of the space between the anterior section 27 and the anterior wall 22. This space will not be used up until the tooth 50 is wedged between the middle of the teeth 40 and the most posterior of the teeth 40 (i.e., the rest position). Thus, the shelf life position is designed to prevent accidental loading of the dispenser in the event that the inner compressible member 18 is accidentally engaged.

In addition, in the shelf-life position, a rib 19 will be exposed to view (see FIG. 2) indicating to the user that the device has never been used before. If rib 19 is not exposed as in FIG. 2, the purchaser will know that the cartridge has been previously used, and possibly tampered with. This is because once the cartridge has been used for the first time, it cannot be placed back into the shelf-life position due to the engagement of the second surface of the tooth 50 of the lever with the second surface of the middle one of the teeth 40 in the rest position (see FIG. 3), or engagement of one-way stop member 54 with a tooth 55. As can be seen from the drawings, one-way stop member 54 is angled such that it permits sliding of the first surface of the tooth 55 inward (i.e., anteriorly), but engages the second surface of tooth 55 in the rest position to prevent return of the inner member 18 to the shelf-life position.

The lower anterior section of housing 16 includes a forwardly projecting finger 57 which extends from the housing 16 in the anterior direction beyond anterior wall 22. The finger 57 can be an integral extension of housing 17, in which case it is preferably covered with a soft sleeve (not illustrated) for engaging the eye. The finger is preferably coated with a material such as Kraton.

The housing 16 may include a cover 58 for closing the aperture 24 which ordinarily exposes the nozzle 2. The cover 58 is swingable by a hinge 59 which is rotatably mounted on a hinge pin 60, which in turn is supported by the side walls 12 of the housing.

It should be appreciated that one advantage of the cartridge of the invention is that the motion which is used to depress the push button 54 and thereby release a drop is in the same direction as the motion used to lower the eyelid and expose the cul-de-sac with finger 57. Therefore, more accurate delivery of the drop is possible. Furthermore, an area of low sensitivity and low tear turn over is specifically targeted by the cartridge which prevents tearing and blinking reflex for better efficacy.

In addition, there is no danger of poking the eyeball with the nozzle 2 since the motion to depress the trigger is not in the direction of the eye, since the nozzle is preferably receded within housing 16, and since the finger 57 extends beyond the nozzle. Moreover, when the trigger is depressed, the return mechanism of the vial projects the inner cylinder 18 in the direction away from the eye. The cartridge is particularly useful for arthritic patients because the push button mechanism allows for easy release of a drop.

In the foregoing specification, the invention has been described with reference to specific exemplary embodiments thereof. It will, however, be evident that various modifications and changes may be made thereunto without departing from the broader spirit and scope of the invention as set forth in the appended claims. For example, the teeth 40 may be replaced with a plurality of notches defined in outer surface of inner member 18, the notches being engageable with tooth 50. Alternatively, teeth 40 may be retained as described herein and tooth 50 may be replaced with a notch which is engageable with teeth 40. The specification and drawings are accordingly to be regarded in an illustrative rather than a restrictive sense.

What is claimed is:

1. A cartridge for use with a dispenser for applying medicament to an eye comprising:
   a housing defining a first aperture in an anterior region thereof, the first aperture for exposing a nozzle of the dispenser to permit medicament from the dispenser to be emitted through said aperture;
   a compressible inner member situated within the housing, the inner member being compressible from an expanded state to a compressed state and the inner member being biased to expand it to said expanded state from said compressed state, the inner member having a region thereof projecting from a second aperture defined by the housing in the expanded state of the inner member;
   a lever which is movable between a first position in engagement with the inner compressible member, and a second position out of engagement with the inner compressible member; and
   a means belonging to the lever or the inner compressible member for retaining the inner compressible member in the compressed state, said means for retaining being disengaged upon movement of the lever from the first position to the second position.

2. The cartridge according to claim 1 wherein the means for retaining includes a tooth belonging to the inner member.

3. The cartridge according to claim 1 wherein the means for retaining includes a tooth belonging to the lever.

4. The cartridge according to claim 2 wherein the means for retaining further includes a tooth belonging to the lever.

5. The cartridge according to claim 1 wherein the lever is pivotable about a pivot axis.

6. The cartridge according to claim 5 wherein the lever includes a pair of prongs coupled to an arm at the pivot axis.

7. The cartridge according to claim 6 wherein the prongs are wedged between members fixedly supported by the housing.

8. The cartridge according to claim 7 wherein an upper one of the pair of prongs includes a raised region which is exposed through a third aperture defined by the housing.

9. The cartridge according to claim 8 wherein the lever further includes a pair of laterally projecting pins, each pin being rotatably mounted in a respective bearing supported by the housing.

10. The cartridge according to claim 9 wherein the means for retaining includes a tooth belonging to the lever arm.

11. The cartridge according to claim 10 wherein the means for retaining further includes a plurality of teeth belonging to the inner member.

12. The cartridge according to claim 1 wherein the inner compressible member includes a spring portion for biasing the member toward its expanded state.

13. The cartridge according to claim 1 further comprising a stop member for retaining the inner compressible member within the housing.

14. The cartridge according to claim 1 further comprising an anteriorly projecting finger which projects from a lower region of the housing.

15. The cartridge according to claim 8 further comprising an anteriorly projecting finger which projects from a lower region of the housing, wherein the lever is situated in an upper region of the housing.

16. The cartridge according to claim 4 wherein each of the tooth belonging to the inner member and the tooth belonging to the lever includes at least a first surface and a second surface, the first surfaces being inclined such that the first surface of the tooth belonging to the inner member may be slid past the first surface of the tooth belonging to the lever upon compression of the inner member, and the second surface of the tooth belonging to the lever engaging the second surface of the tooth belonging to the inner member in the compressed state of the inner member so as to retain the inner member in the compressed state.

17. The cartridge according to claim 11 wherein each of the teeth belonging to the inner member and the tooth belonging to the lever includes at least a first surface and a second surface, the first surfaces being inclined such that the first surfaces of the teeth belonging to the inner member may be slid past the first surface of the tooth belonging to the lever upon compression of the inner member, and the second surface of the tooth belonging to the lever engaging the second surfaces of the teeth belonging to the inner member in the compressed state of the inner member so as to retain the inner member in the compressed state.

18. The cartridge according to claim 14 wherein the means for retaining comprises a plurality of teeth belonging to the inner member and a tooth belonging to the lever, and wherein each of the teeth belonging to the inner member and the tooth belonging to the lever includes at least a first surface and a second surface, the first surfaces being inclined such that the first surfaces of the teeth belonging to the inner member may be slid past the first surface of the tooth belonging to the lever upon compression of the inner member, and the second surface of the tooth belonging to the lever engaging the second surface of one of the teeth belonging to the inner member in the compressed state of the inner member so as to retain the inner member in the compressed state.

19. The cartridge according to claim 15 wherein the means for retaining comprises a plurality of teeth belonging to the inner member and a tooth belonging to the lever, and wherein each of the teeth belonging to the inner member and the tooth belonging to the lever includes at least a first surface and a second surface, the first surfaces being inclined such that the first surfaces of the teeth belonging to the inner member may be slid past the first surface of the tooth belonging to the lever upon compression of the inner member, and the second surface of the tooth belonging to the lever engaging the second surface of one of the teeth belonging to the inner member in the compressed state of the inner member so as to retain the inner member in the compressed state.

20. The cartridge according to claim 1 further comprising a cover coupled to the housing, the cover being movable between a first position in which it closes the first aperture and a second position in which the first aperture is open.

21. A cartridge in combination with a dispenser for applying medicament to an eye, the dispenser being of the type which is actuated to load a drop of medicament into a drop cavity therein by compression in its longitudinal direction to a compressed position and which is actuated to emit said drop from a nozzle upon subsequent longitudinal expansion from said compressed position under the action of a biasing means, the cartridge comprising:
- a housing retaining the dispenser therein, the housing defining a first aperture for exposing the nozzle of the dispenser;
- an inner telescoping member slidably received within the housing for compressing the dispenser in its longitudinal direction, the inner telescoping member having a portion thereof projecting to the exterior of the housing through a second aperture defined therein;
- a means for locking the inner telescoping member in a position where the dispenser is in the compressed position; and
- a lever for disengaging the means for locking to allow the dispenser to expand from said compressed position to said expanded position by the action of the biasing means.

22. The cartridge combination according to claim 21 further comprising a finger for engaging an eyelid, the finger projecting from the housing to extend beyond an anterior end of the housing.

23. The cartridge combination according to claim 21 wherein the inner telescoping member seals a portion of the dispenser from the external environment.

* * * * *